(12) United States Patent
Backus et al.

(10) Patent No.: US 10,213,299 B2
(45) Date of Patent: Feb. 26, 2019

(54) VALVE DELIVERY SYSTEM WITH PINLESS RELEASE MECHANISM

(71) Applicant: BOSTON SCIENTIFIC SCIMED, INC., Maple Grove, MN (US)

(72) Inventors: Andrew J. H. Backus, San Francisco, CA (US); Randy S. Gamarra, Santa Clara, CA (US); Crissly V. Crisostomo, Folsom, CA (US); Takashi H. Ino, San Jose, CA (US)

(73) Assignee: BOSTON SCIENTIFIC SCIMED INC., Maple Grove, MN (US)

( * ) Notice: Subject to any disclaimer, the term of this patent is extended or adjusted under 35 U.S.C. 154(b) by 96 days.

(21) Appl. No.: 15/216,772

(22) Filed: Jul. 22, 2016

(65) Prior Publication Data

US 2017/0027688 A1    Feb. 2, 2017

Related U.S. Application Data

(60) Provisional application No. 62/197,711, filed on Jul. 28, 2015.

(51) Int. Cl.
*A61F 2/24* (2006.01)
*A61F 2/90* (2013.01)
*A61F 2/95* (2013.01)

(52) U.S. Cl.
CPC ............ *A61F 2/243* (2013.01); *A61F 2/2436* (2013.01); *A61F 2/90* (2013.01); *A61F 2002/9534* (2013.01); *A61F 2220/0033* (2013.01)

(58) Field of Classification Search
CPC ..................... A61F 2/243; A61F 2/2436; A61F 2220/0033; A61F 2002/9534; A61F 2/90;
(Continued)

(56) References Cited

U.S. PATENT DOCUMENTS

| 2007/0112355 A1* | 5/2007 | Salahieh | ............... A61F 2/2418 606/108 |
| 2010/0121434 A1* | 5/2010 | Paul | ......................... A61F 2/24 623/2.11 |
| 2012/0016469 A1 | 1/2012 | Salahieh et al. | |

FOREIGN PATENT DOCUMENTS

| WO | 2010042950 A2 | 4/2010 |
| WO | 2010117680 A1 | 10/2010 |

OTHER PUBLICATIONS

International Search Report and Written Opinion, PCT/US2016/043490, dated Oct. 4, 2016.

* cited by examiner

*Primary Examiner* — Darwin Erezo
*Assistant Examiner* — Erich Herbermann
(74) *Attorney, Agent, or Firm* — Seager, Tufte & Wickhem LLP.

(57) ABSTRACT

Medical devices and methods for making and using medical devices are disclosed. An example medical device may include an inner shaft having a distal end region. A valve implant may be releasably coupled to the distal end region. The valve implant may be capable of shifting between an elongated configuration and an expanded configuration. A post assembly may be disposed along the valve implant. The post assembly may include a release member that is axially slidable along the post assembly. The medical device may also include a rod designed to engage the release member. The rod may be designed to shift the valve implant between the elongated configuration and the expanded configuration. Axially shifting the release member along the post assembly may release the rod from the post assembly and deploy the valve implant.

14 Claims, 13 Drawing Sheets

(58) Field of Classification Search
CPC .... A61F 2002/9522; A61F 2/07; A61F 2/954; A61B 17/12118
See application file for complete search history.

VALVE DELIVERY SYSTEM WITH PINLESS RELEASE MECHANISM

RELATED APPLICATIONS

This application claims the benefit of U.S. Provisional Application No. 62/197,711, filed Jul. 28, 2015.

TECHNICAL FIELD

The present disclosure pertains to medical devices and methods for making and using medical devices. More particularly, the present disclosure pertains to medical devices for delivering a valve implant.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device is disclosed. The medical device comprises:
 an inner shaft having a distal end region;
 a valve implant releasably coupled to the distal end region;
 wherein the valve implant is capable of shifting between an elongated configuration and an expanded configuration;
 a deployment sheath capable of being disposed about the valve implant when the valve implant is in the elongated configuration;
 a post assembly disposed along the valve implant;
 wherein the post assembly includes a release member that is axially slidable along the post assembly;
 a rod designed to engage the release member, wherein the rod is designed to shift the valve implant between the elongated configuration and the expanded configuration; and
 wherein axially shifting the release member along the post assembly releases the rod from the post assembly and deploys the valve implant.

Alternatively or additionally to any of the embodiments above, the valve implant is a replacement aortic valve.

Alternatively or additionally to any of the embodiments above, the release member is a clevis pin extending through at least a portion of the post assembly.

Alternatively or additionally to any of the embodiments above, the rod has a forked distal end region.

Alternatively or additionally to any of the embodiments above, the post assembly has a side opening.

Alternatively or additionally to any of the embodiments above, the forked distal end region of the rod includes a projection that is designed to extend through the side opening.

Alternatively or additionally to any of the embodiments above, the post assembly includes a second side opening, wherein the forked distal end region of the rod include a second projection, and wherein the second projection is designed to extend through the second side opening.

Alternatively or additionally to any of the embodiments above, a buckle member is coupled to the valve implant.

Alternatively or additionally to any of the embodiments above, the buckle member is designed to engage the release member and cause the release member to axially shift along the post assembly.

Another example medical device is disclosed. The medical device comprises:
 an inner shaft having a distal end region;
 a valve implant releasably coupled to the distal end region;
 a post assembly disposed along the valve implant;
 a release member axially slidable along the post assembly;
 a rod for shifting the valve implant between a delivery configuration and a deployment configuration, the rod being capable of engaging the release member; and
 wherein axially shifting the release member along the post assembly releases the rod from the post assembly and deploys the valve implant.

Alternatively or additionally to any of the embodiments above, the valve implant is a replacement aortic valve.

Alternatively or additionally to any of the embodiments above, the release member is a clevis pin extending through at least a portion of the post assembly.

Alternatively or additionally to any of the embodiments above, the rod has a forked distal end region.

Alternatively or additionally to any of the embodiments above, the post assembly has a side opening.

Alternatively or additionally to any of the embodiments above, the forked distal end region of the rod includes a projection that is designed to extend through the side opening.

Alternatively or additionally to any of the embodiments above, the post assembly includes a second side opening, wherein the forked distal end region of the rod include a second projection, and wherein the second projection is designed to extend through the second side opening.

Alternatively or additionally to any of the embodiments above, a buckle member is coupled to the valve implant.

Alternatively or additionally to any of the embodiments above, the buckle member is designed to engage the release member and cause the release member to axially shift along the post assembly.

An example method for delivering a valve implant is disclosed. The method comprises:
 advancing a delivery system through a body lumen to a position adjacent a target site, the delivery system comprising:
  an inner shaft having a distal end region,
  a valve implant releasably coupled to the distal end region,
  a post assembly disposed along the valve implant,
  a release member axially slidable along the post assembly,
  a rod for shifting the valve implant between a delivery configuration and a deployment configuration, the rod being capable of engaging the release member, and
 proximally retracting the rod to begin shifting the valve implant from the delivery configuration toward the deployment configuration;
 assessing the positioning of the valve implant relative to the target site; and
 further proximally retracting the rod to axially shift the release member along the post assembly, release the rod from the post assembly, and complete shifting of the valve implant to the deployment configuration.

Alternatively or additionally to any of the embodiments above, the delivery system includes a handle having an actuation mechanism, and wherein proximally retracting the rod, further proximally retracting the rod, or both include actuating the actuation mechanism.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
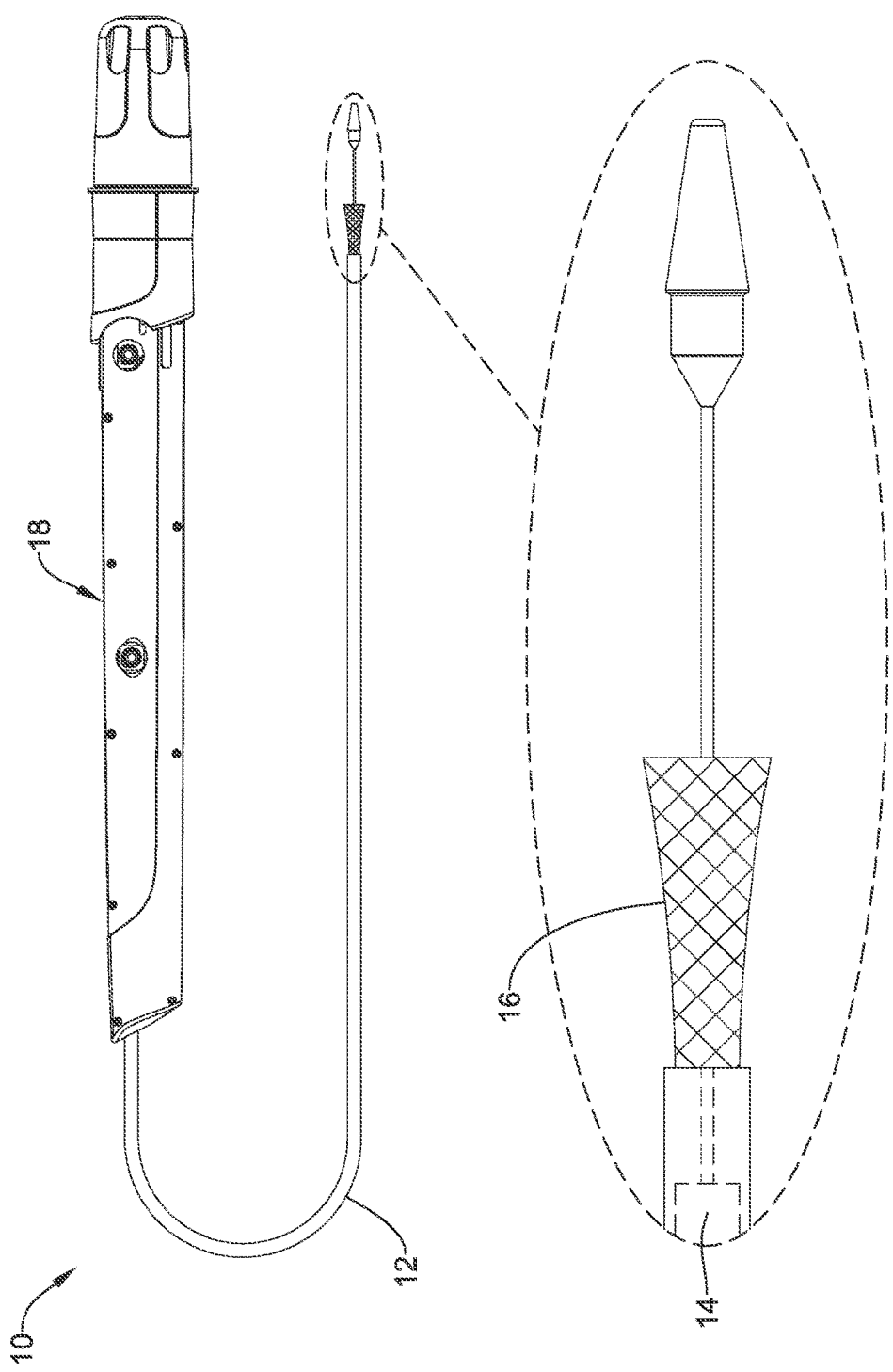
FIG. 1 is side view of an example medical device system.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Diseases and/or medical conditions that impact the cardiovascular system are prevalent in the United States and throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Some relatively common medical conditions may include or be the result of inefficiency, ineffectiveness, or complete failure of one or more of the valves within the heart. For example, failure of the aortic valve can have a serious effect on a human and could lead to serious health condition and/or death if not dealt with. Treatment of defective heart valves poses other challenges in that the treatment often requires the repair or outright replacement of the defective valve. Such therapies may be highly invasive to the patient. Disclosed herein are medical devices that may be used for delivering a medical device to a portion of the cardiovascular system in order to diagnose, treat, and/or repair the system. At least some of the medical devices disclosed herein may be used to deliver and implant a replacement heart valve (e.g., a replacement aortic valve). In addition, the devices disclosed herein may deliver the replacement heart valve percutaneously and, thus, may be much less invasive to the patient. The devices disclosed herein may also provide a number of additional desirable features and benefits as described in more detail below.

FIG. 1 is a side view of an example medical device system 10. It should be noted that some features of system 10 are either not shown, or are shown schematically, in FIG. 1 for simplicity. Additional details regarding some of the components of system 10 are provided in other figures in greater detail. System 10 may be used to deliver and/or deploy a variety of medical devices to a number of locations within the anatomy. In at least some embodiments, system 10 is a replacement heart valve delivery system (e.g., a replacement aortic valve delivery system) that can be used for percutaneous delivery of a replacement heart valve. This, however, is not intended to be limiting as system 10 may also be used for other interventions including mitral valve replacement, valve repair, valvuloplasty, and the like, or other similar interventions.

System 10 may generally be described as a catheter system that includes an outer sheath or catheter 12 and an inner catheter or tube 14 (a portion of which is shown in FIG. 1 in phantom line) extending at least partially through outer sheath 12. A medical device implant 16 may be coupled to inner catheter 14 and disposed within outer sheath 12 during delivery of implant 16. A handle 18 may be disposed at the proximal end of outer sheath 12 and inner catheter 14. In general, handle 18 may be configured to manipulate the position of outer sheath 12 relative to inner catheter 14 as well as aid in the deployment of implant 16.

In use, system 10 may be advanced percutaneously through a body lumen or cavity (e.g., the vasculature) to a position adjacent to an area of interest. For example, system 10 may be advanced through the vasculature to a position adjacent to a defective aortic valve. During delivery, implant 16 may be generally disposed in an elongated and low profile "delivery" configuration within outer sheath 12. Once positioned, outer sheath 12 may be retracted to expose implant 16. Implant 16 may be actuated in order to expand implant into a generally shortened and larger profile "deployed" configuration suitable for implantation within the anatomy. When implant 16 is suitably deployed within the anatomy, system 10 can be removed from the vasculature, leaving implant 16 in place to function as, for example, a suitable replacement for the native aortic valve. In at least some interventions, implant 16 may be deployed within the native valve (e.g., the native valve is left in place and not excised). Alternatively, the native valve may be removed and implant 16 may be deployed in its place as a replacement.

Figure 2:
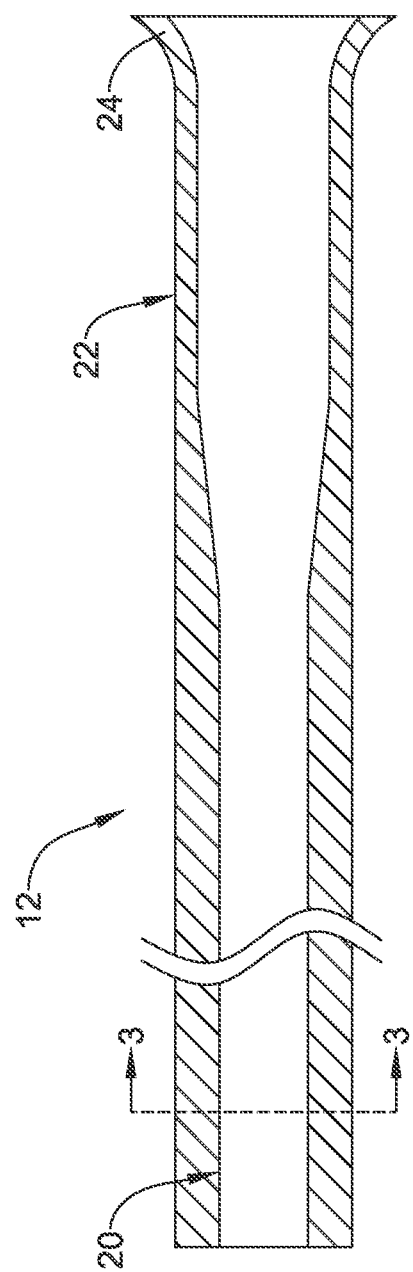
FIG. 2 is a cross-sectional side view of an example outer sheath.

FIGS. 2-7 illustrate some of the components of system 10. For example, FIG. 2 is a cross-sectional side view of outer sheath 12. Here it can be seen that outer sheath 12 has a proximal portion 20 and a distal portion 22. Distal portion 22 may have a slightly enlarged or flared inner diameter, which may provide additional space for holding implant 16 therein. For example, the inner diameter of outer sheath 12 along proximal portion 20 may be in the range of about 0.254 to 1.27 cm (0.10 to 0.50 inches), or about 0.508 to 1.016 cm (0.20 to 0.40 inches), or about 0.508 to 0.762 cm (0.20 to 0.30 inches), or about 0.56388±0.0508 cm (0.222±0.002 inches). The inner diameter of outer sheath 12 along distal portion 22 may be in the range of about 0.254 to 1.27 cm (0.10 to 0.50 inches), or about 0.508 to 1.016 cm (0.20 to 0.40 inches), or about 0.508 to 0.762 cm (0.20 to 0.30 inches), or about 0.579 to 0.5842 cm (0.228 to 0.230 inches). At the distal end of distal portion 22 may be a distal tip 24, which may be flared or otherwise have a funnel-like shape. The funnel-like shape increases the outer diameter (and inner diameter) of outer sheath 12 at distal tip 24 and may aid in the sheathing and/or resheathing of implant 16 into outer sheath 12. Other than at distal tip 24, outer sheath 12 may have a generally constant outer diameter. For example, outer sheath 12 may have an outer diameter in the range of about 0.254 to 1.27 cm (0.10 to 0.50 inches), or about 0.508 to 1.016 cm (0.20 to 0.40 inches), or about 0.508 to 0.762 cm (0.20 to 0.30 inches), or about 0.6858 cm (0.270 inches). These are just examples. Other embodiments are contemplated that have differing dimensions (including those appropriate for differently sized patients including children) and/or arrangements for the outer diameter and/or inner diameter of outer sheath 12. These contemplated embodiments include outer sheaths with flared or otherwise variable outer diameters, embodiments with constant inner diameters, combinations thereof, and the like. Outer sheath 12 may also have a length that is appropriate for reaching the intended area of interest within the anatomy. For example, outer sheath 12 may have a length in the range of about 30 to 200 cm, or about 60 to 150 cm, or about 100 to 120 cm, or about 108±0.20 cm. Outer sheath 12 may also be curved. For example, a distal section of outer sheath 12 may be curved. In one example, the radius of the curve (measured from the center of outer sheath 12) may be in the range of about 2 to 6 cm (20 to 60 mm), or about 3 to 4 cm (30 to 40 mm), or about 3.675 cm (36.75 mm). Again, these dimensions are examples and are not intended to be limiting.

Figure 3:
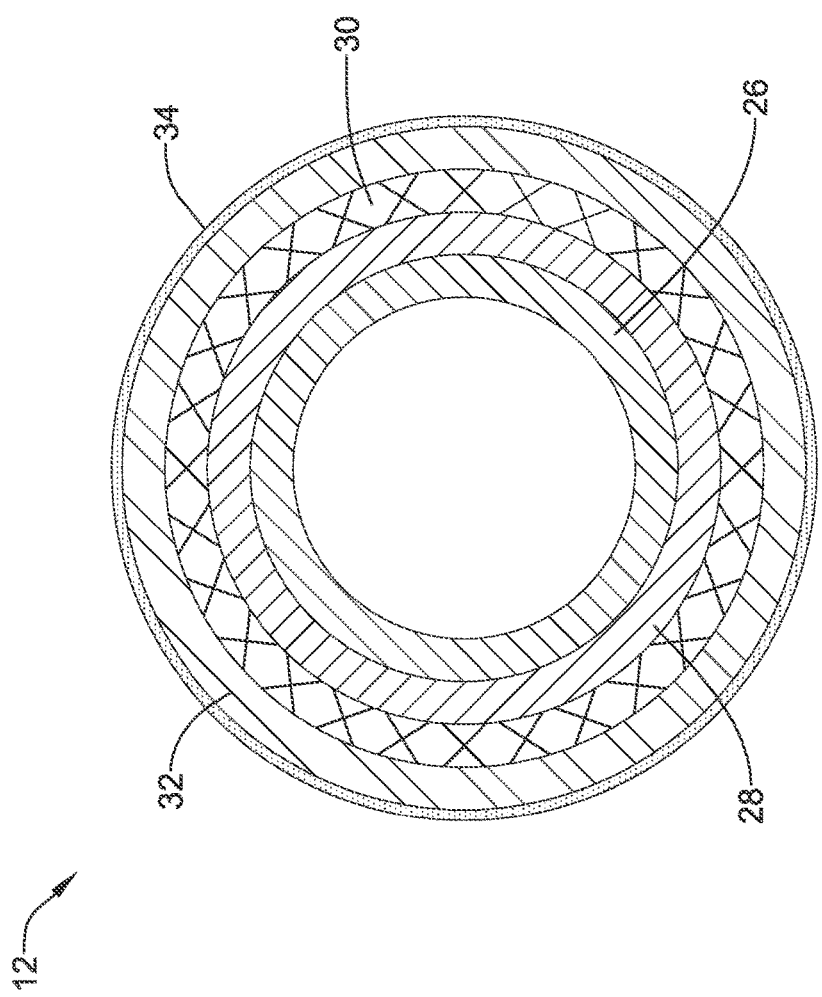
FIG. 3 is a transverse cross-sectional view taken through line 3-3 in FIG. 2.

Outer sheath 12 may be formed from a singular monolithic tube or unitary member. Alternatively, outer sheath 12 may include a plurality of layers or portions. One or more of these layers may include a reinforcing structure such as a braid, coil, mesh, combinations thereof, or the like. FIG. 3 illustrates one example of a multilayer structure for outer sheath 12. For example, outer sheath 12 may include an inner liner or layer 26. An intermediate or tier layer 28 may be disposed on inner liner 26. A reinforcement 30 may be disposed on intermediate layer 28. A topcoat or outer layer 32 may be disposed on reinforcement 30. Finally, an outer coating 34 (e.g., a lubricious coating, a hydrophilic coating, a hydrophobic coating, etc.) may be disposed along portions or all of topcoat 32. These are just examples. Several alternative structural configurations are contemplated for outer sheath 12 including embodiments including two or more layers that may be different from those shown in FIG. 3, embodiments without a reinforcement, and the like, or other suitable configurations.

The dimensions and materials utilized for the various layers of outer sheath 12 may also vary. For example, inner liner 26 may include a polymeric material such as fluorinated ethylene propylene (FEP) and may have a thickness in the range of about 0.00254 to 0.0127 cm (0.001 to 0.005 inches) or about 0.00762±0.00254 (0.003±0.001 inches), intermediate layer 28 may include a polymer material such as polyether block amide (e.g., PEBAX 6333) and may have a thickness in the range of about 0.00254 to 0.0127 cm (0.001 to 0.005 inches) or about 0.00508±0.00254 (0.002±0.001 inches), outer coating 34 may include a polymer material such as polyether block amide (e.g., PEBAX 7233) and may have a thickness in the range of about 0.00254 to 0.0254 cm (0.001 to 0.01 inches). In some embodiments, outer coating 34 may vary in thickness. For example, along proximal portion 20 outer coating 34 may have greater thickness, such as about 0.0127 to about 0.0508 cm or about 0.02159 cm (0.005 to 0.02 inches or about 0.0085 inches), than along distal portion 22 and/or distal tip 24, which may be about 0.0127 to about 0.0508 cm or about 0.01651 cm (e.g., about 0.005 to 0.02 inches or about 0.0065 inches). These are just examples as other suitable materials may be used.

The form of distal tip 24 may also vary. For example, in at least some embodiments, inner liner 26 (i.e., a 2.5 mm section thereof) may be extended up and around the distal end of outer sheath 12 (e.g., around reinforcement 30 and topcoat 32). A ring member (not shown) made from a suitable material such as a 55D polyether block amide (e.g., 55D PEBAX) may be disposed over inner liner 26 and heat bonded to form distal tip 24. This may form the funnel-like shape of distal tip 24.

Reinforcement 30 may also vary in form. In at least some embodiments, reinforcement 30 may take the form of a braid, coil, mesh, or the like. For example, in some embodiments, reinforcement 30 may include a metallic braid (e.g., stainless steel). In some of these embodiments, reinforcement 30 may also include additional structures such as one or more longitudinally-extending strands. For example, reinforcement 30 may include a pair of longitudinally-extending aramid and/or para aramid strands (for example, KEVLAR®) disposed on opposite sides of the braid. These strands may or may not be woven into portions or all of the braid.

Figure 4:
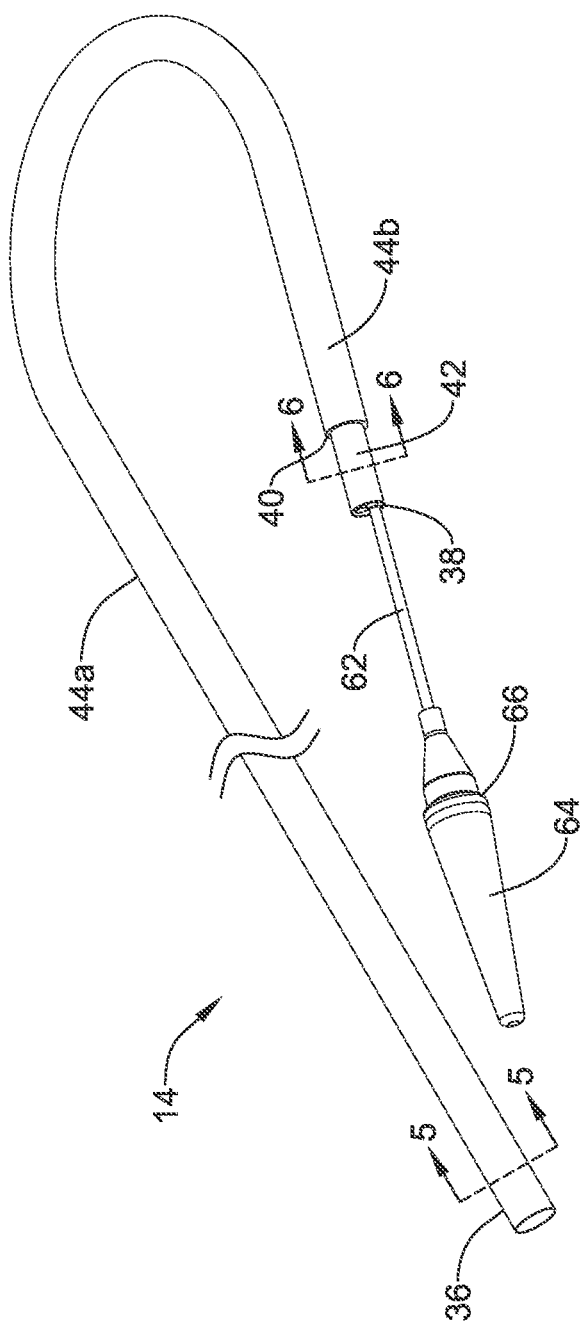
FIG. 4 is a side view of an example inner catheter.
Figure 5:
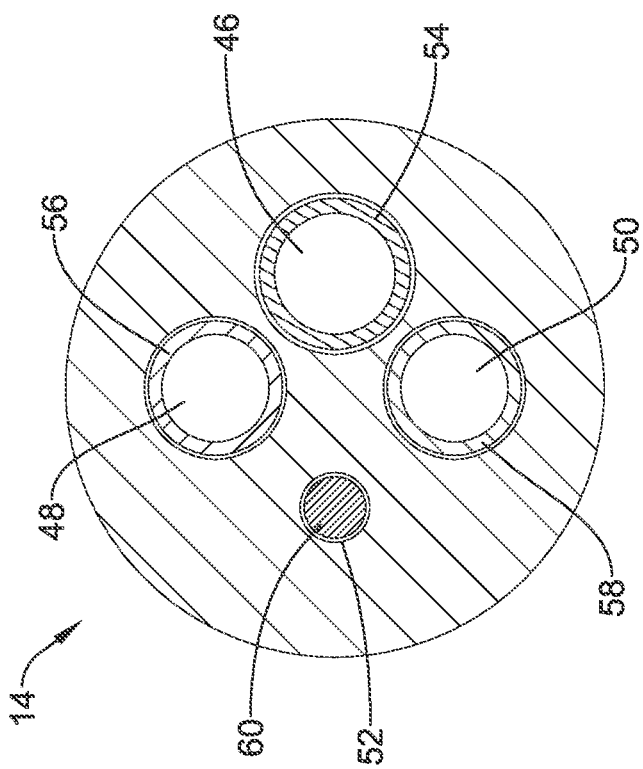
FIG. 5 is a cross-sectional view taken through line 5-5 in FIG. 4.

FIG. 4 is a side view of the inner catheter 14. A distal end region of inner catheter 14 may include a step in outer diameter 40 that defines a decreased outer diameter section 42. For example, decreased outer diameter section 42 may have an outer diameter in the range of about 0.127 to 0.635 cm (0.05 to 0.25 inches), or about 0.254 to 0.508 cm (0.10 to 0.20 inches), or about 0.38608±0.00762 (0.152±0.003 inches) as opposed to the remainder of inner catheter 14 where the outer diameter may be in the range of about 0.127 to 0.762 cm (0.05 to 0.30 inches), or about 0.254 to 0.635 cm (0.10 to 0.25 inches), or about 0.508±0.0254 cm (0.20±0.01 inches). Decreased outer diameter section 42 may define a region where other components of system 10 may be attached. Some additional details regarding these components can be found herein.

In general, inner catheter 14 may take the form of an extruded polymer tube. Other forms are also contemplated including other polymer tubes, metallic tubes, reinforced tubes, or the like including other suitable materials such as those disclosed herein. In some embodiments, inner catheter 14 is a singular monolithic or unitary member. In other embodiments, inner catheter 14 may include a plurality of portions or segments that are coupled together. The total length of inner catheter may be in the range of about 60 to 150 cm, or about 80 to 120 cm, or about 100 to 115 cm, or about 112±0.02 cm. Just like outer sheath 12, inner catheter 14 may also be curved, for example adjacent to the distal end thereof. In some embodiments, inner catheter 14 may have one or more sections with a differing hardness/stiffness (e.g., differing shore durometer). For example, inner catheter may have a proximal region 44a and an intermediate region 44b. Proximal region 44a may include a generally stiff polymeric material such as a 72D polyether block amide (e.g., 72D PEBAX) and may have a length in the range of about 60 to 150 cm, or about 80 to 120 cm, or about 100 to 115 cm, or about 109.5±0.02 cm. Intermediate region 44b may include a 40D polyether block amide (e.g., 40D PEBAX) and may have a length in the range of about 5 to 25 mm, or about 10 to 20 mm, or about 15±0.01 mm. Section 42 may also differ from regions 44a/44b and, in some embodiments, may include a 72D polyether block amide (e.g., 72D PEBAX) and may have a length in the range of about 0.5 to 2 cm (5 to 20 mm), or about 0.8 to 1.5 cm (8 to 15 mm), or about 1±0.001 cm (10±0.01 mm). These are just examples.

Figure 6:
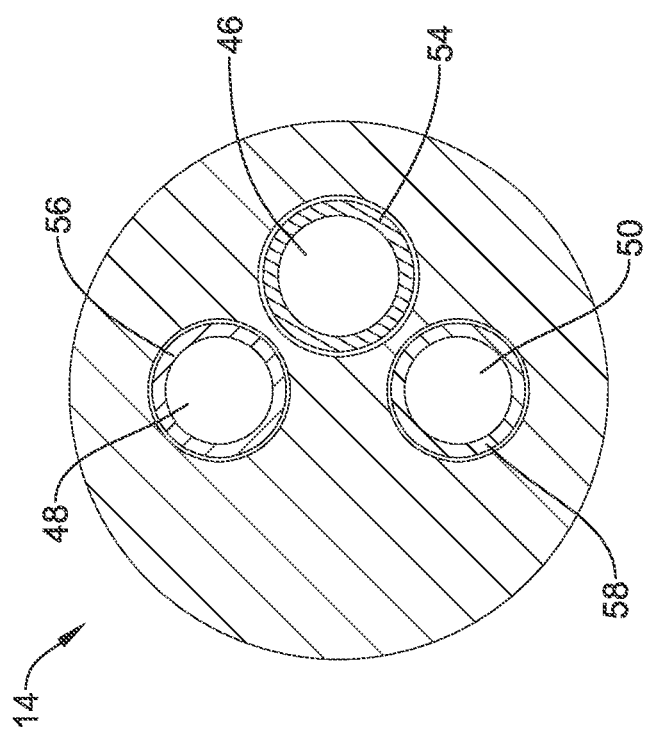
FIG. 6 is a cross-sectional view taken through line 6-6 in FIG. 4.

Inner catheter 14 may include one or more lumens. For example, FIG. 5 (which is a cross sectional view of inner catheter 14 adjacent to proximal end portion 36) illustrates that inner catheter 14 may include a first lumen 46, a second lumen 48, a third lumen 50, and a fourth lumen 52. In general, lumens 46/48/50/52 extend along the entire length of inner catheter 14. Other embodiments are contemplated, however, where one or more of lumens 46/48/50/52 extend along only a portion of the length of inner catheter 14. For example, fourth lumen 52 may stop just short of the distal end of inner catheter 14 and/or be filled in at its distal end to effectively end fourth lumen 52 proximal of the distal end of inner catheter 14, as illustrated in FIG. 6 by the absence of fourth lumen 52 adjacent to the distal end of inner catheter 14.

Disposed within first lumen 46 may be push-pull rods 84 (not shown in FIG. 5, seen in other figures including FIG. 7), which are used to expand and/or elongate implant 16 as explained in more detail herein. In at least some embodiments, first lumen 46 may be lined with a low friction liner 54 (e.g., a FEP liner). Disposed within second lumen 48 may be a pin release mandrel 92 (not shown in FIG. 5, seen in other figures including FIG. 7). In at least some embodiments, second lumen 48 may be lined with a hypotube liner 56. Third lumen 50 may be a guidewire lumen and this lumen may also be lined with a hypotube liner 58.

Fourth lumen 52 may be used to house a non-stretch wire 60. The form of non-stretch wire 60 may vary. In some embodiments, non-stretch wire 60 may take the form of a stainless steel braid. The non-stretch wire 60 may optionally include a pair of longitudinally-extending aramid and/or para aramid strands (for example, KEVLAR®) disposed on opposite sides of the braid. In general, rather than being "disposed within" fourth lumen 52, non-stretch wire 60 may be embedded within fourth lumen 52. In addition, non-stretch wire 60 may extend to a position adjacent to distal end portion 38 but not fully to the distal end of inner catheter 14 as illustrated in FIG. 6 by the absence of fourth lumen 52 adjacent to the distal end of inner catheter 14. For example, a short distal segment of fourth lumen 52 may be filled in with polymer material adjacent to the distal end of inner catheter 14.

Inner catheter 14 may also include a guidewire extension tube 62 that extends distally from distal end portion 38. A nose cone 64 is attached to guidewire extension tube 62. Nose cone 64 generally is designed to have an atraumatic shape. Nose cone 64 may also include a ridge or ledge 66 that is configured to abut the distal tip 24 of outer sheath 12 during delivery of implant 16.

Figure 7:
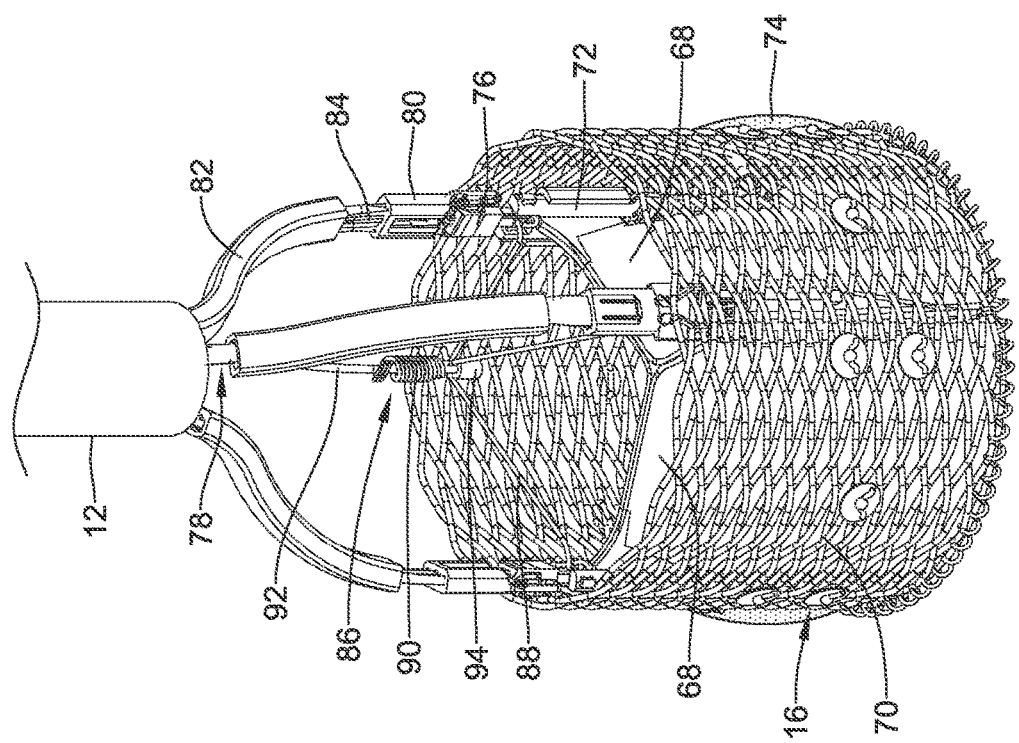
FIG. 7 is a perspective view of a portion of an example implant associated with the example medical device system.

FIG. 7 illustrates some of the additional components of system 10 and implant 16. For example, here it can be seen that implant 16 includes a cylindrical braid 70 and a plurality of valve leaflets 68 (e.g., bovine pericardial) secured to a plurality of post or post assemblies 72, for example at the commissure portions of the leaflets 68. In this example, implant 16 includes three leaflets 68 secured to three post assemblies 72. Leaflets 68 may also be secured to the base or "inflow end" of braid 70. The post assemblies 72, in turn, may be secured to braid 70 (e.g., along the interior of braid 70) with sutures or other suitable mechanisms. Positioned adjacent to (e.g., longitudinally spaced from and aligned with) post assemblies 72 are a plurality of buckles 76, which may also be sutured to braid 70 (e.g., along the interior of braid 70). In this example, one buckle 76 is attached to braid 70 adjacent to each of the three post assemblies 72. Accordingly, in at least some embodiments braid 70 has a total of three buckles 76 and three post assemblies 72 attached thereto. Other embodiments are contemplated where fewer or more buckles 76 and post assemblies 72 may be utilized. A seal 74 (shown in cross-section) may be disposed about braid 70 and, as the name suggests, may help to seal implant 16 within a target implant site or area of interest.

Attachment between implant 16 and inner catheter 14 (and/or outer sheath 12) may be effected through the use of a three finger coupler 78. Coupler 78 may generally include a cylindrical base (not shown) that is attached to inner catheter 14 (e.g., disposed about and attached to reduced outer diameter section 42). Projecting distally from the base are three fingers that are each configured to engage with implant 16 at post assemblies 72 and buckles 76. A collar 80 may further assist in holding together these structures. A guide 82 may be disposed over each of the fingers and may serve to keep the fingers of coupler 78 associated with push-pull rods 84 extending adjacent to coupler 78. Finally, a pin release assembly 86 may be a linking structure that keeps post assemblies 72, buckles 76, and push-pull rods 84 associated with one another. Pin release assembly 86 includes a plurality of individual pins 88 that may be joined together via a coiled connection 90 and held to a pin release mandrel 92 with a ferrule 94.

During delivery, implant 16 is secured at the distal end of inner catheter 14 by virtue of the association of the fingers of coupler 78 being coupled with a projecting proximal end of buckles 76 (and being held in place with collar 80 disposed over the connection) and by virtue of pins 88 securing together push-pull rods 84 and post assemblies 72. When implant 16 is advanced within the anatomy to the desired location, outer sheath 12 may be withdrawn (e.g., moved proximally relative to inner catheter 14) to expose implant 16. Then, push-pull rods 84 can be used to expand and "lock" implant 16 in the expanded or deployed configuration by proximally retracting push-pull rods 84 to pull post assemblies 72 into engagement with buckles 76. Finally, pins 88 can be removed, thereby uncoupling push-pull rods 84 from post assemblies 72, which allows implant 16 to be released from system 10 and deployed in the anatomy.

The use of pins 88 desirably allows implant 16 to remain secured with system 10 until a clinician decides that it is appropriate to release implant 16. While effective, it may be desirable for other release mechanisms to be utilized that may still allow for controlled release of the implant whiles also simplifying the release process and/or the construction of the delivery system/device. Some example devices/systems are disclosed herein that utilize alternative "pinless" release mechanisms.

FIGS. 8-13 illustrate an example "pinless" release mechanism that may be used with system 10 and/or other systems disclosed and/or contemplated herein. The pinless release mechanism may be desirable for a number of reasons. For example, the pinless release system may simplify the process for delivering and/or deploying an implant (e.g., implant 16). In some instances, the process for deploying the implant may utilize fewer steps. For example, the deployment process may be accomplished using a single knob or actuation member along a handle (e.g., handle 18). In addition, the use of a pinless release system may allow for a pin release assembly (e.g., pin release assembly 86) and handle components designed to interact with the pin release assembly to be omitted from the system. Not only would this simplify the manufacturing of the device and reduce costs, this may allow for portions of system 10 (e.g., outer sheath 12 and/or inner catheter 14) to be manufactured with a lower profile (e.g., due to fewer parts extending along inner catheter 14). Other features and benefits are contemplated.

Figure 8:
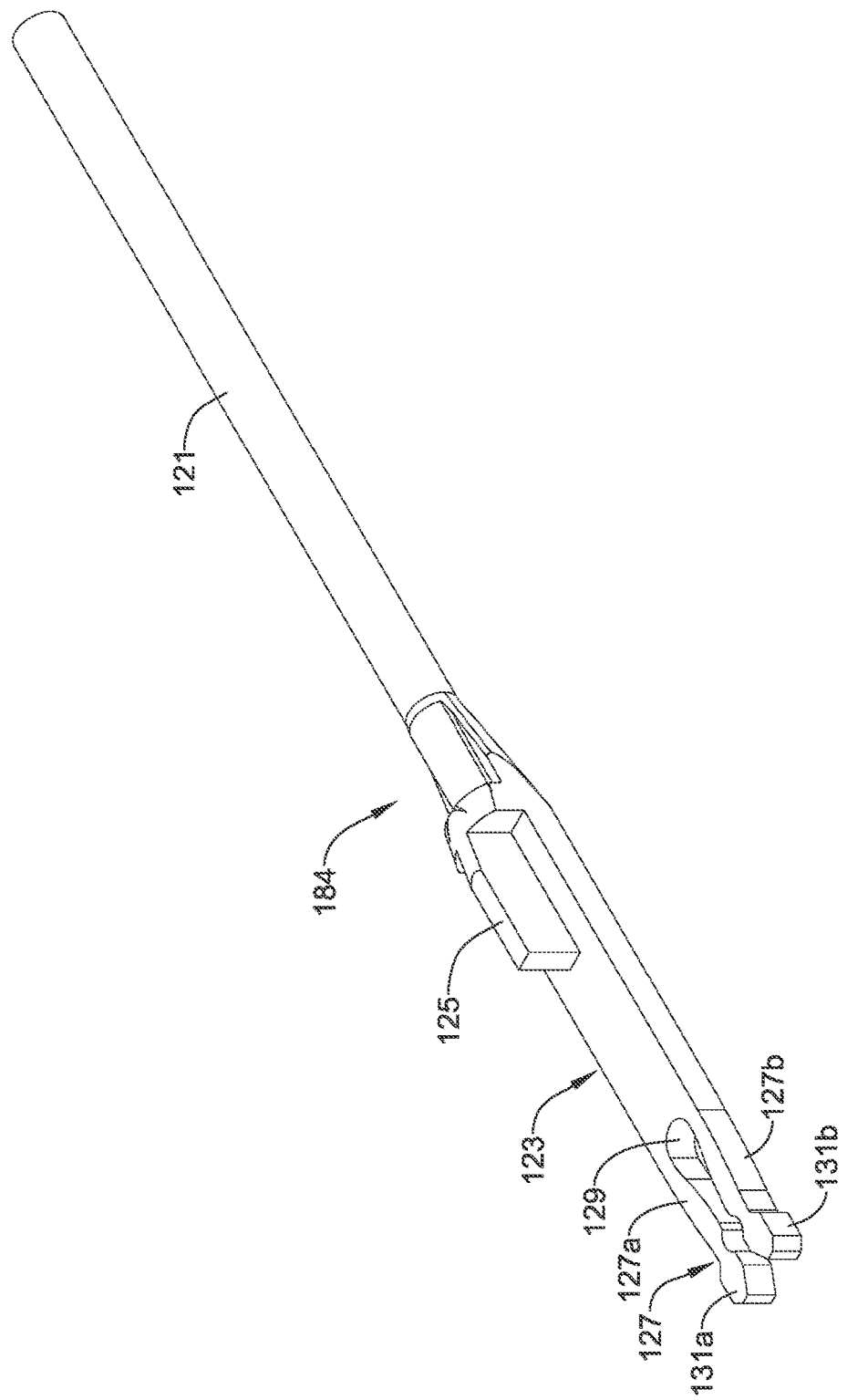
FIG. 8 is a perspective view of the distal end of an example push-pull rod.

FIG. 8 illustrates an example push-pull rod 184 that may be used as part of a pinless release mechanism and that may be similar in form and function to other push-pull rods disclosed herein. In some instances, three push-pull rods 184 may be used to deploy an implant (e.g., implant 16). However, other numbers of push-pull rods 184 are contemplated including, for example, one, two, four, five, six, or more. Push-pull rod 184 has a shaft portion 121 and a distal portion 123. A ridge 125 may be disposed along distal portion 123. Generally, push-pull rod 184 (e.g., distal portion 123) may be designed to be slidable within inner catheter 14 (e.g., within first lumen 46 of inner catheter 14). In some instances, shaft portion 121 may have a round or circular cross-sectional shape. In other instances, shaft portion 121 may have a ribbon-like shape that is non-circular in cross-sectional shape. For example, shaft portion 121 may have a rectangular cross-sectional shape. Other shapes are contemplated.

Push-pull rod 184 may have a forked end region 127 defining forks or arms 127a/127b. An opening or channel 129 may be defined between arms 127a/127b. Arms 127a/127b may be flexible such that they can flex inwardly and outwardly. In other words, arms 127a/127b can flex in and out such that opening 129 becomes smaller and larger, respectively. The ends of arms 127a/127b may include projections 131a/131b, which can be engaged with a post assembly as described in more detail herein.

Figure 9:
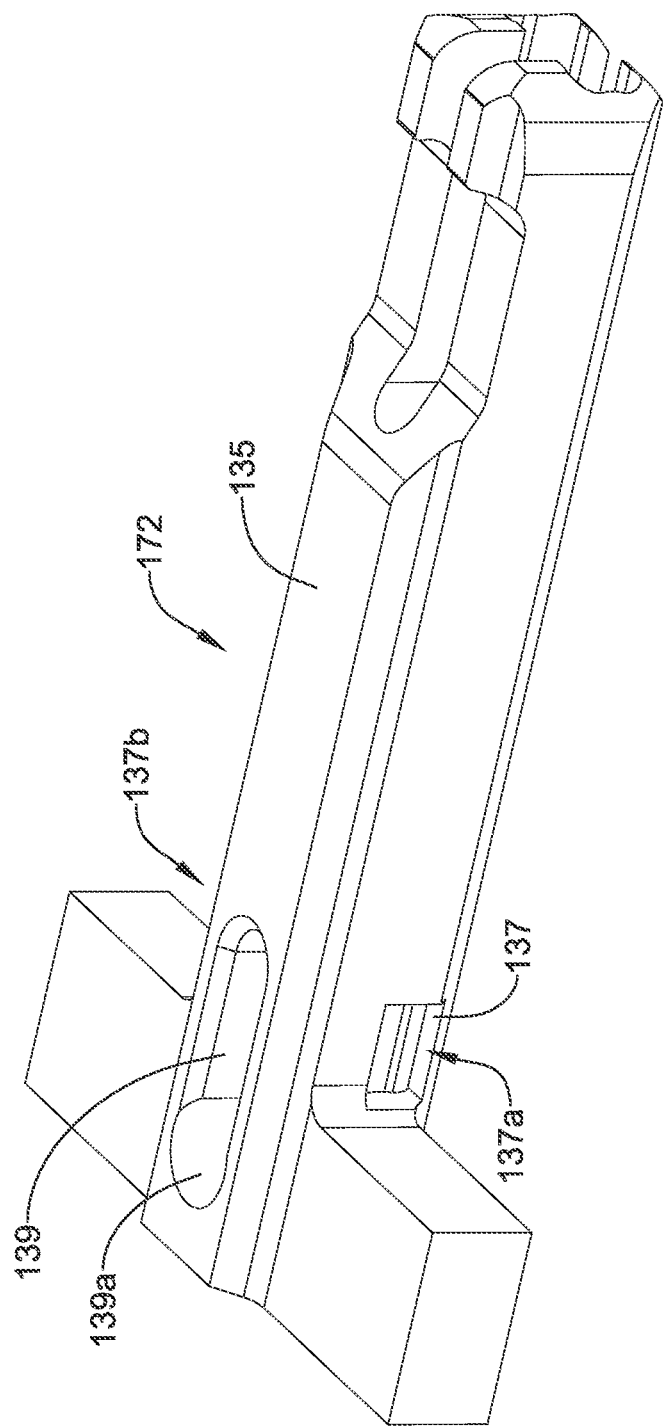
FIG. 9 is a perspective view of an example post top.

FIG. 9 illustrates a portion of an example post assembly 172 that may be similar in form and function to other post assemblies disclosed herein. Assembly 172 may include post top 135 and post legs (e.g., post legs 141a/141b; not shown in FIG. 9 but can be seen in FIGS. 11-13). One or more windows or openings 137 that extend laterally, may be defined along the sides of post top 135 including, for example, openings 137a/137b. A top hole or opening 139 may also be formed in post top 135. In at least some instances, a region 139a of opening 139 may be enlarged.

Figure 10:
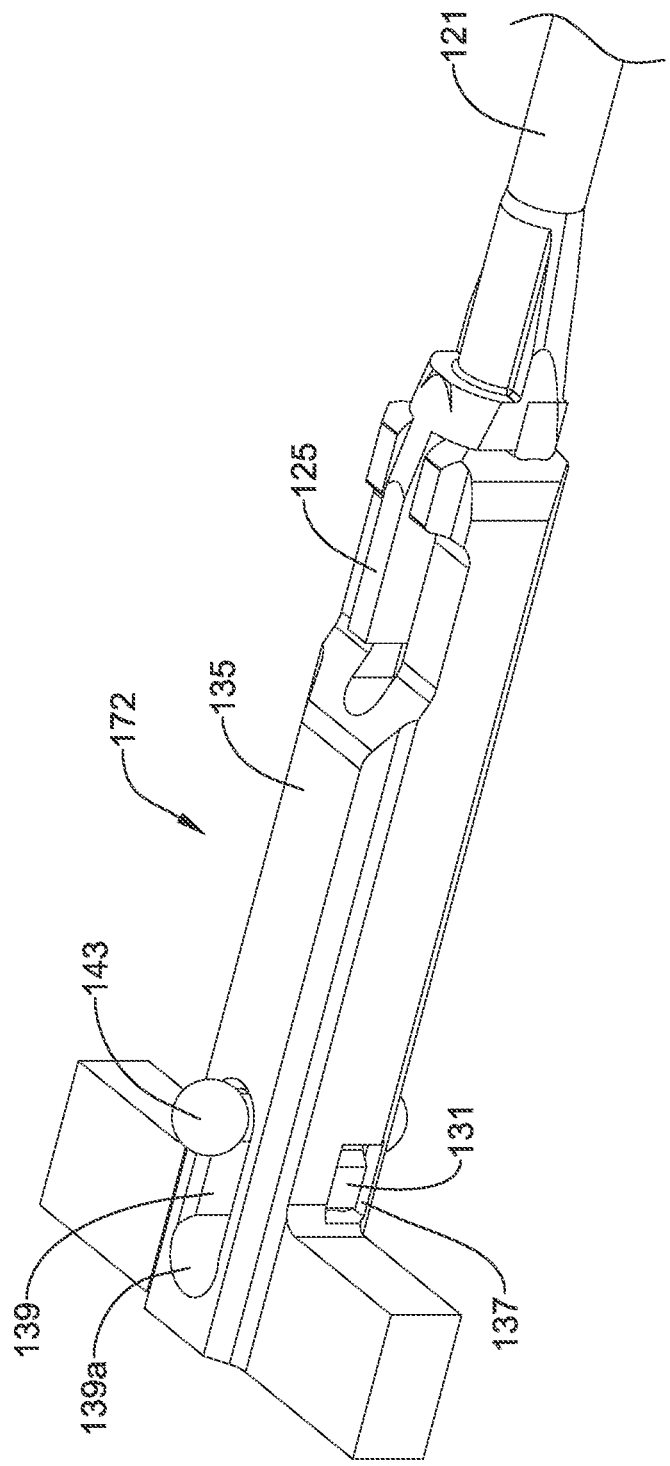
FIG. 10 is a perspective view of an example post top engaged with a push-pull rod.

FIG. 10 illustrates push-pull rod 184 engaged with post top 135. Here, arms 127a/127b extend through a bore within post top 135 and are disposed about a release member 143. In this example, release member 143 takes the form of a clevis pin. Clevis pin 143 is axially movable within opening 139. In other words, clevis pin 143 is able to axially shift within opening 139. Projections 131a/131b are disposed within and extend at least partially through openings 137a/137b (e.g., in FIG. 10, projection 131 can be seen projecting through opening 137). When so configured, clevis pin 143 is positioned between arms 127a/127b. Arms, however, are prevented by post top 135 from opening up any wider in order to allow push-pull rod 184 to be separated from post top 135. Thus, in this configuration, push-pull rod 184 is secured to post top 135.

Figure 11:
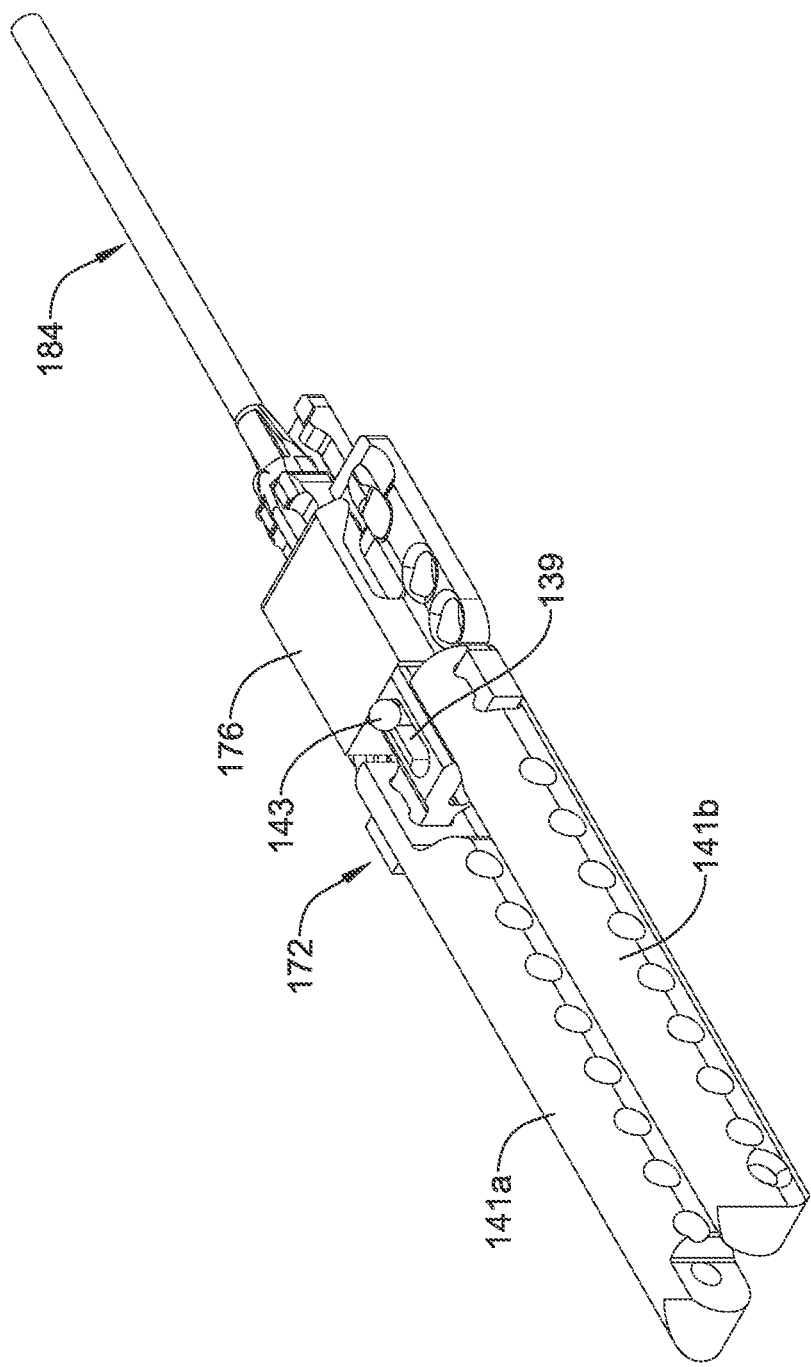
FIG. 11 is a perspective view of an example post top, push-pull rod, and buckle.
Figure 12:
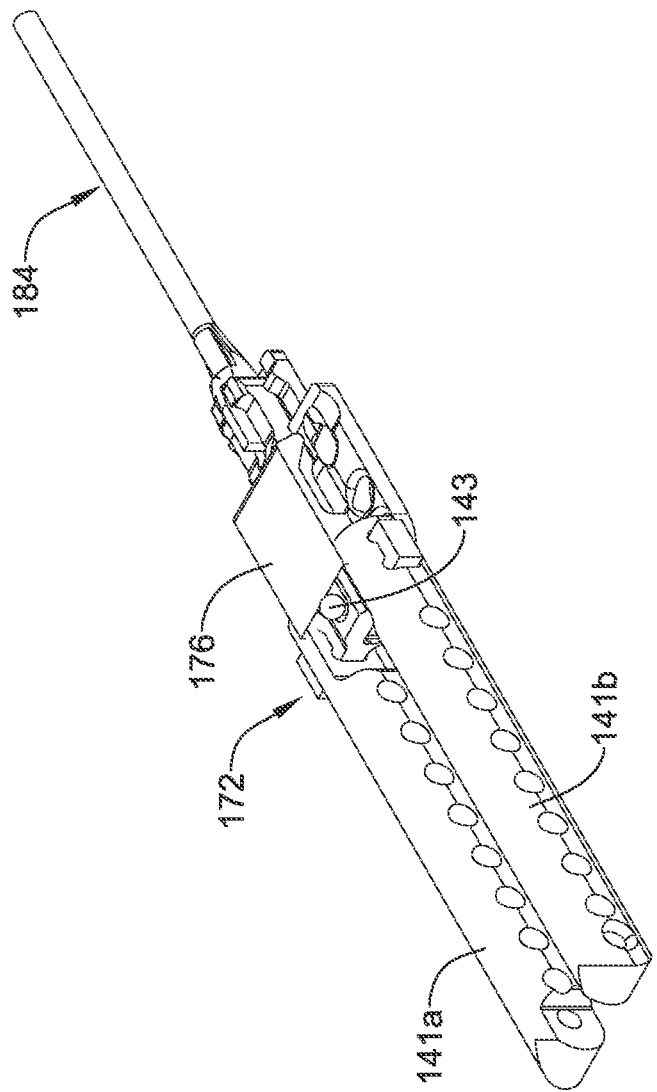
FIG. 12 is a perspective view of a buckle engaging an example release member.
Figure 13:
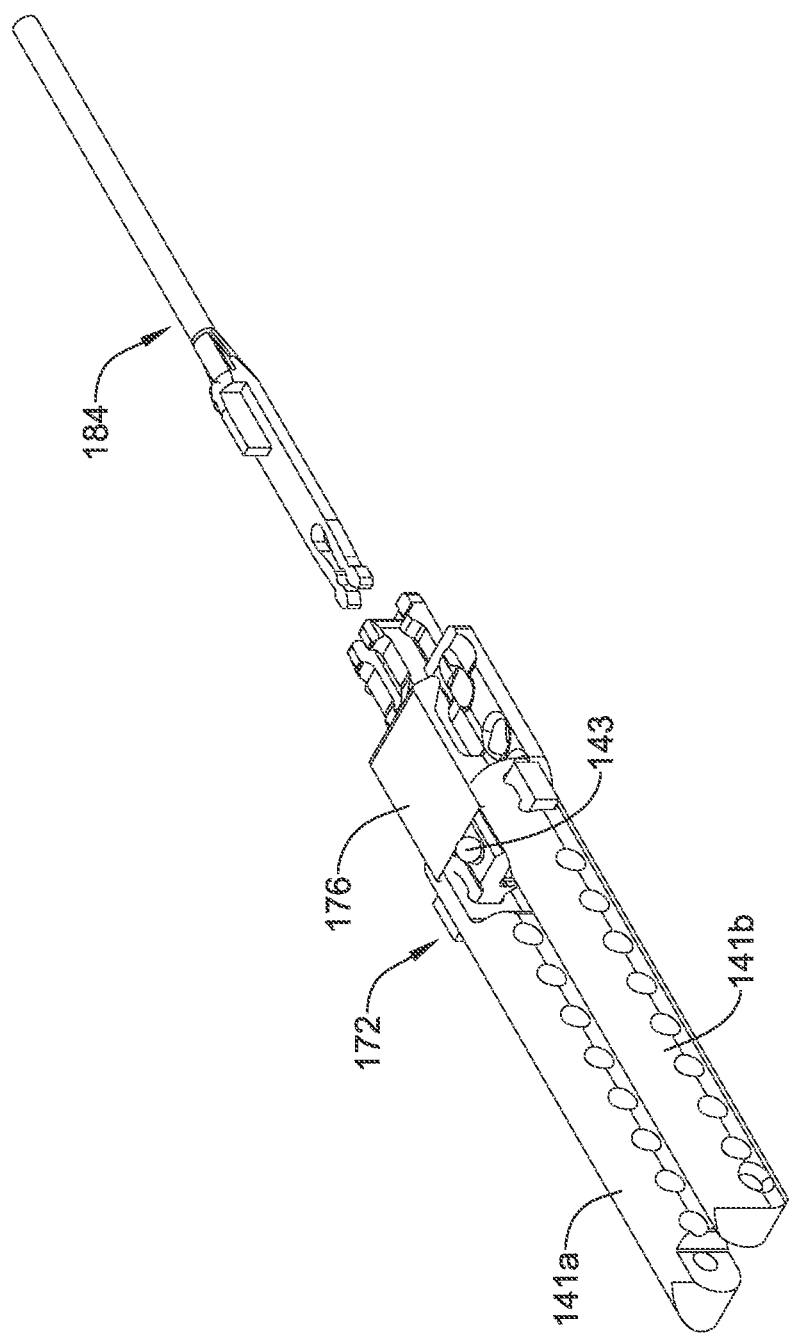
FIG. 13 is a perspective view of an example push-pull rod releasing from the post assembly.

FIGS. 11-13 illustrate the release of push-pull rod 184 from post top 135. FIG. 11 illustrates push-pull rod 184 engaged with post assembly 172 and also shows post legs 141a/141b secured to post assembly 172. When push-pull rod 184 is pulled proximally, post assembly 172 moves toward a buckle 176. When release member 143 engages buckle 176, further proximal retraction of push-pull rod 184 cause release member 143 to axially slide within opening 139 as shown in FIG. 12. When this happens, release member 143 may be pulled or otherwise released from projections 131a/131b, which allows push-pull rod 184 to be pulled out from and released from post top 135 as shown in FIG. 13.

Proximally retracting push-pull rod 184 may be accomplished using an actuation mechanism disposed along or otherwise within a handle (e.g., handle 18). For example, the handle may include a knob that is designed to be rotated. When the knob is rotated, the actuation mechanism may move (e.g., using a lead screw, one or more carriages, and/or the like), causing push-pull rod 184 to move.

U.S. Pat. No. 8,951,299, U.S. Patent Application Pub. No. US 2013/0123912, and U.S. Patent Application Pub. No. US 2014/0114405 are herein incorporated by reference in their entirety.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A medical device, comprising:
an inner shaft having a distal end region;
a valve implant releasably coupled to the distal end region;
wherein the valve implant is capable of shifting between an elongated configuration and an expanded configuration;
a deployment sheath capable of being disposed about the valve implant when the valve implant is in the elongated configuration;
a post assembly disposed along the valve implant;
wherein the post assembly includes a release member that is axially slidable within an opening in the post assembly, wherein a portion of the release member extends through the post assembly;
a rod designed to engage the release member, wherein the rod is designed to shift the valve implant between the elongated configuration and the expanded configuration; and
wherein shifting the portion of the release member extending through the post assembly from a first axial position within the post assembly to a second axial position within the post assembly releases the rod from the post assembly and deploys the valve implant;
wherein the rod has a forked distal end region.

2. The medical device of claim 1, wherein the valve implant is a replacement aortic valve.

3. The medical device of claim 1, wherein the release member is a clevis pin extending through at least a portion of the post assembly.

4. The medical device of claim 1, wherein the post assembly has a side opening extending through a side wall of the post assembly.

5. The medical device of claim 4, wherein the forked distal end region of the rod includes a projection that is designed to extend through the side opening.

6. The medical device of claim 5, wherein the post assembly includes a second side opening, wherein the forked distal end region of the rod includes a second projection, and wherein the second projection is designed to extend through the second side opening.

7. The medical device of claim 1, wherein a buckle member is coupled to the valve implant, the buckle member being configured to receive at least a portion of the post assembly therein.

8. A medical device, comprising:
an inner shaft having a distal end region;
a valve implant releasably coupled to the distal end region;
wherein the valve implant is capable of shifting between an elongated configuration and an expanded configuration;
a deployment sheath capable of being disposed about the valve implant when the valve implant is in the elongated configuration;
a post assembly disposed along the valve implant;
wherein the post assembly includes a release member that is axially slidable within an opening in the post assembly, wherein a portion of the release member extends through the post assembly;
a rod designed to engage the release member, wherein the rod is designed to shift the valve implant between the elongated configuration and the expanded configuration; and
wherein shifting the portion of the release member extending through the post assembly from a first axial position within the post assembly to a second axial position within the post assembly releases the rod from the post assembly and deploys the valve implant;
wherein a buckle member is coupled to the valve implant, the buckle member being configured to receive at least a portion of the post assembly therein;
wherein the buckle member is designed to engage the release member and cause the portion of the release member extending through the post assembly to shift from a first axial position within the post assembly to a second axial position within the post assembly.

9. A medical device, comprising:
an inner shaft having a distal end region;
a valve implant releasably coupled to the distal end region;
a post assembly disposed along the valve implant;
a release member engaged with and axially slidable within an opening in the post assembly;
a rod for shifting the valve implant between a delivery configuration and a deployment configuration, the rod being capable of engaging the release member; and
wherein axially shifting the release member along the post assembly releases the rod from the post assembly and deploys the valve implant;
wherein the release member remains engaged with the post assembly after the rod is released from the post assembly;
wherein the release member is a clevis pin extending through at least a portion of the post assembly;
wherein the rod has a forked distal end region, wherein the post assembly has a side opening extending laterally from an axial lumen of the post assembly.

10. The medical device of claim 9, wherein the valve implant is a replacement aortic valve.

11. The medical device of claim 9, wherein the forked distal end region of the rod includes a projection that is designed to extend through the side opening.

12. The medical device of claim 11, wherein the post assembly includes a second side opening, wherein the forked distal end region of the rod includes a second projection, and wherein the second projection is designed to extend through the second side opening.

13. The medical device of claim 9, wherein a buckle member is coupled to the valve implant, the buckle member being configured to receive at least a portion of the post assembly therein.

14. The medical device of claim 13, wherein the buckle member is designed to engage the release member and cause the release member to axially shift along the post assembly.

* * * * *